US005703049A

United States Patent [19]
Rao
[11] Patent Number: 5,703,049
[45] Date of Patent: Dec. 30, 1997
[54] HIGH METHIONINE DERIVATIVES OF α-HORDOTHIONIN FOR PATHOGEN-CONTROL

[75] Inventor: Aragula Gururaj Rao, Urbandale, Iowa

[73] Assignee: Pioneer Hi-Bred Int'l, Inc., Des Moines, Iowa

[21] Appl. No.: 608,786

[22] Filed: Feb. 29, 1996

[51] Int. Cl.$^6$ .......... A61K 38/00

[52] U.S. Cl. .......... 514/12; 514/2; 530/324

[58] Field of Search .......... 514/2, 12; 530/324

[56] References Cited

U.S. PATENT DOCUMENTS 5,258,300 11/1993 Glassman et al. .......... 435/240.4

FOREIGN PATENT DOCUMENTS

WO 94/16078 7/1994 WIPO .

OTHER PUBLICATIONS

Burow, et al. "Suppression of phaseolin and lectin in seeds of common bean, *Phaseolus volgaris* L.: increased accumulation of 54 kDa polypeptides is not associated with higher seed methionine concentrations", (1993).

Rao, et al. "Synthesis and Characterization of Defensin NP-1" *Int. J. Peptide Protein Res.*; vol 40; pp. 507–514; (1992).

Berry–Lowe, et al. "The Nucleotide Sequence, Expression, and Evolution of One Member of a Multigene Family Encoding the Small Subunit of Ribulose–1,5–Bisphosphate Carboxylase in Soybean" *J. of Mol. and Applied Genetics*; vol. 1; pp. 483–498; (1982).

Cashmore, "Nuclear Genes Encoding the Small Subunit of Ribulose–1,5–Bisphosphate Carboxylase"; *An Agricultural Perspective*; pp. 29–38; (1983).

Coruzzi, et al. "Nucleotide Sequences of Two Pea cDNA Clones Encoding the Small Subunit of Ribulosse 1,5–Bisphosphate Carboxylase and the Major Chlorophyll a/b–binding Thylakoid Polypeptide" *J. Biological Chemistry*; vol. 258(3): pp. 1399–1042; (1983).

Dunsmuir, et al. "The Major Chlorophyll a/b Binding Protein of Petunia is Composed of Several Polypeptides Encoded by a Number of Distinct Nuclear Genes"; vol. 2; pp. 285–300; (1983).

Florack et al., 24 Plant. Mol. Biol. 83–96 (1994).

Brummer et al., 219 Eur. J. Biochem. 425–433 (1994).

Rao et al., 7(12) Prot. Engineer. 1485–93 (1994).

Matthews et al., in Biochemistry. pp. 137–141, The Benjamin Cummings Publishing Company, Inc., NY (1990).

*Primary Examiner*—Robert A. Wax
*Assistant Examiner*—Einar Stole

[57] ABSTRACT

Derivatives of α-hordothionin made by position-specific substitution with methionine residues provide methionine enrichment in plants while retaining the anti-pathogenic activity of the parent compound.

10 Claims, No Drawings

HIGH METHIONINE DERIVATIVES OF α-HORDOTHIONIN FOR PATHOGEN-CONTROL

TECHNICAL FIELD

This invention relates to the improvement of feed formulations. Specifically, this invention relates to derivatives of α-hordothionin which provide higher percentages of the essential amino acid methionine in plants, while retaining the anti-pathogenic functionality of hordothionins.

BACKGROUND OF THE INVENTION

Feed formulations are required to provide animals essential nutrients critical to growth. However, crop plants are generally rendered food sources of poor nutritional quality because they contain low proportions of several amino acids which are essential for, but cannot be synthesized by, animals.

For many years, researchers have attempted to improve the balance of essential amino acids in the proteins of important crops through breeding programs. As more becomes known about storage proteins and the expression of the genes which encode these proteins, and as transformation systems are developed for a greater variety of plants, molecular approaches for improving the nutritional quality of seed proteins can provide alternatives to the more conventional approaches. Thus, specific amino acid levels can be enhanced in a given crop via biotechnology.

One alternative method is to express a heterologous protein of favorable amino acid composition at levels sufficient to obviate food or feed supplementation. For example, a number of seed proteins rich in sulfur amino acids have been identified. A key to good expression of such proteins involves efficient expression cassettes with seed specific promoters. Not only must the gene-controlling regions direct the synthesis of high levels of mRNA, the mRNA must be translated into stable protein.

Among the essential amino acids needed for animal nutrition, often missing from crop plants, are methionine, threonine and lysine. Attempts to increase the levels of these free amino acids by breeding, mutant selection and/or changing the composition of the storage proteins accumulated in crop plants has met with minimal success. Usually, the expression of the transgenic storage protein is too low. The phaseolin-promoted Brazil nut 2S expression cassette is an example of an effective chimeric seed-specific gene. However, even though Brazil nut protein increases the amount of total methionine and bound methionine, thereby improving nutritional value, there appears to be a threshold limitation as to the total amount of methionine that is accumulated in the seeds. The seeds remain insufficient as sources of methionine.

An alternative to the enhancement of specific amino acid levels by altering the levels of proteins containing the desired amino acid is modification of amino acid biosynthesis. Recombinant DNA and gene transfer technologies have been applied to alter enzyme activity catalyzing key steps in the amino acid biosynthetic pathway. Glassman, U.S. Patent No. 5,258,300; Galili, et al.; European Patent Application No. 485970; (1992); incorporated herein in its entirety by reference. However, modification of the amino acid levels in seeds is not always correlated with changes in the level of proteins that incorporate those amino acids. Burrow, et al, *Mol. Gen. Genet.;* Vol. 241; pp. 431–439; (1993); incorporated herein in its entirety by reference.. Although significant increases in free lysine levels in leaves have been obtained by selection for DHDPS mutants or by expressing the *E. coli* DHDPS in plants, it remains to be shown that these alterations can increase bound target amino acids, which represent some 90% or more of total amino acids. Thus, there is minimal impact on the nutritional value of seeds.

In addition to increasing the nutritional value of feed formulations, disease resistance and control is an important objective of the genetic engineering of crop plants. Numerous pathogens, including fungi and bacteria, are significant pests of common agricultural crops.

One method of controlling disease caused by such pathogens has been to apply anti-microbial organic or semi-organic chemicals to crops. This method has numerous art-recognized problems.

A second method of controlling pathogens has been the use of biological control organisms which are typically natural competitors or inhibitors of the pathogens. However, it is difficult to apply biological control organisms to large areas, and even more difficult to cause the living organisms to remain in the treated area for an extended period.

A third method is the use of recombinant DNA techniques to insert cloned genes into plant cells wherein the genes express anti-microbial compounds. This technology has given rise to additional concerns about eventual microbial resistance to well-known, naturally occurring anti-microbials, particularly in the face of heavy selection pressure, which may occur in some areas. Thus, a continuing effort is under way to express naturally occurring anti-microbial compounds in plant cells directly by translation of a single structural gene.

It is especially important that while crops produce adequate levels of anti-microbial compounds, they continue to produce plant products for nutritional purposes. Unfortunately, plant cells can only produce large quantities of a few cellular components at a time. Thus, if they are producing high levels of storage proteins, for example, it is difficult for them to also produce high levels of anti-microbial compounds. Genetic engineers therefore face a quandary in designing advanced plant systems with existing molecules for nutrition quality enhancement and disease resistance which require concurrent high-level expression of multiple genes.

Based on the foregoing, there exists a need for methods of increasing the levels of the essential amino acids methionine, lysine and threonine in plants, while maintaining any anti-microbial activity existing in the plants.

It is therefore an object of the present invention to provide methods for genetically modifying plants to increase the levels of the essential amino acid methionine in the plants, while maintaining any anti-microbial activity existing in the plants.

DISCLOSE OF THE INVENTION

It has now been determined that one class of compounds, the α-hordothionins, can be modified to enhance their content of methionine while maintaining their anti-microbial activity. These hordothionin derivatives can be expressed to simultaneously enhance both resistance to pathogenic diseases and methionine content of the plant.

α-hordothionin is a 45-amino acid protein which has been well characterized. It can be isolated from seeds of barley (*Hordeum vulgare*). The molecule is stabilized by four disulfide bonds resulting from eight cysteine residues. The amino acid sequence is as provided in SEQUENCE I.D. No.

1. It has powerful anti-microbial properties. In its native form, the protein is especially rich in arginine and lysine residues, containing 5 residues (10%) of each. However, it is devoid of the essential amino acid methionine.

The protein has been synthesized and the three-dimensional structure determined by computer modeling. The modeling of the protein predicts that the ten charged residues (arginine at positions 5,10,17,19 and 30, and lysine at positions 1,23,32,38 and 45) all occur on the surface of the molecule. The side chains of the polar amino acids (asparagine at position 11, glutamine at position 22 and threonine at position 41) also occur on the surface of the molecule. Furthermore, the hydrophobic amino acids, (such as the side chains of leucine at positions 8,15,24 and 33 and valine at position 18) are also solvent-accessible.

Three-dimensional modeling of the protein indicates that the arginine residue at position 10 is critical to retention of the appropriate 3-dimensional structure and possible folding through hydrogen bond interactions with the C-terminal residue of the protein. A methionine substitution at that point would disrupt the hydrogen bonding involving arginine at position 10, serine at position 2 and lysine at position 45, leading to a destabilization of the structure. The synthetic peptide having this substitution could not be made to fold correctly, which supported this analysis. Conservation of the arginine residue at position 10 provided a protein which folded correctly.

Since methionine is a hydrophobic amino acid, the surface hydrophobic amino acid residues, leucine at positions 8,15, and 33, and valine at position 18, were substituted with methionine. The surface polar amino acids, asparagine at position 11, glutamine at position 22 and threonine at position 41, are substituted with methionine. The resulting compound has the sequence indicated in SEQUENCE I.D. No. 2. The molecule is synthesized by solid phase peptide synthesis and folds into a stable structure. It has seven methoinine residues (15.5%) and, including the eight cysteines, the modified protein has a sulfur amino acid content of 33%.

While SEQUENCE I.D. No. 2 is illustrative of the present invention, it is not intended to be a limitation. Methionine substitutions can also be performed at positions containing charged amino acids. Only arginine at position 10 is critical for maintaining the structure of the protein through a hydrogen-bonding network with serine at position 2 and lysine at position 45. Thus, one can substitute methionine for lysine at positions 1,23,32, and/or 38, and for arginine at positions 5,17,19 and/or 30. The resulting compound has the sequence indicated in SEQUENCE I.D. No. 3.

Synthesis of the compounds is performed according to methods of peptide synthesis which are well known in the art and thus constitute no part of this invention. In vitro, the compounds have been synthesized on an applied Biosystems model 431a peptide synthesizer using fastmoc™ chemistry involving hbtu [2-(1h-benzotriazol-1-yl)-1,1,3,3-tetramethyluronium hexafluoro-phosphate, as published by Rao, et al., *Int. J. Pep. Prot. Res.;* Vol. 40; pp. 508–515; (1992); incorporated herein in its entirety by reference. Peptides were cleaved following standard protocols and purified by reverse phase chromatography using standard methods. The amino acid sequence of each peptide was confirmed by automated edman degradation on an applied biosystems 477a protein sequencer/120a pth analyzer. More preferably, however, the compounds of this invention are synthesized in vivo by bacterial or plant cells which have been transformed by insertion of an expression cassette containing a synthetic gene which when transcribed and translated yields the desired compound. Such empty expression cassettes, providing appropriate regulatory sequences for plant or bacterial expression of the desired sequence, are also well-known, and the nucleotide sequence for the synthetic gene, either RNA or DNA, can readily be derived from the amino acid sequence for the protein using standard reference texts. Preferably, such synthetic genes will employ plant-preferred codons to enhance expression of the desired protein.

Industrial Applicability

The following description further exemplifies the compositions of this invention and the methods of making and using them. However, it will be understood that other methods, known by those of ordinary skill in the art to be equivalent, can also be employed.

The polypeptides employed in this invention can be effectively applied to plants afflicted with susceptible microorganisms by any convenient means, including spray, creams, dust or other formulation common to the anti-microbial arts. The compound can also be incorporated systematically into the tissues of a treated plant so that in the course of infesting the plant the pathogens will be exposed to anti-microbial amounts of a compound of this invention. One method of doing this is to incorporate the compound in a non-phytotoxic vehicle which is adapted for systemic administration to the susceptible plants. This method is commonly employed with fungicidal materials such as captan and is well within the purview of one of ordinary skill in the art of plant fungicide formulation. However since the genes which code for these compounds can be inserted into an appropriate expression cassette and introduced into cells of a susceptible plant species, an especially preferred embodiment of this method involves inserting into the genome of the plant a DNA sequence coding for a compound of this invention in proper reading frame, together with transcription initiator and promoter sequences active in the plant. Transcription and translation of the DNA sequence under control of the regulatory sequences causes expression of the protein sequence at levels which provide an anti-microbial amount of the protein in the tissues of the plant which are normally infected by the pathogens.

The plant is preferably a plant susceptible to infection and damage by one or more of *Fusarium graminearum*, *Fusarium moniliforme*, *Aspergillus flavus*, *Alternaria longipes*, *Sclerotinia sclerotiorum*, and *Sclerotina trifoliorum*. These include corn (*Zea mays*) and sorghum (*Sorghum bicolor*). However, this is not to be construed as limiting, inasmuch as these two species are among the most difficult commercial crops to reliably transform and regenerate, and these pathogens also infect certain other crops. Thus the methods of this invention are readily applicable via conventional techniques to numerous plant species, if they are found to be susceptible to the plant pathogens listed hereinabove, including, without limitation, species from the genera *Allium, Antirrhinum, Arabidopsis, Arachis, Asparagus, Atropa, Arena, Beta, Brassica, Browallia, Capsicum, Cicer, Cicla, Citrullus, Citrus, Cucumis, Cucurbita, Datura daucus, Digitalis, Fagopyrum, Fragaria, Geranium, Glycine, Gossypium, Helianthus, Hordeum, Hemerocallis, Lactuca, Lens, Lolium, Lotus, Lycopersicon, Majorana, Manihot, Medicago, Nasturtium, Nicotiana, Oryza, Pelargonium, Persea, Petunia, Phaseolus, Pisum, Ranunculus, Raphanus, Ricinus, Saccharum, Secale, Senecio, Setaria, Solanum, Spinacia, Trifolium, Triticum, Bromus, Cichorium, Hyoscyamus, Linum, Nemesia, Panicum, Onobrychis, Pennisetum, Salpiglossis, Sinapis, Trigonella,* and *Vigna.*

The genes which code for the present compounds can be inserted into an appropriate expression cassette and introduced into cells of a plant species. Thus, an especially preferred embodiment of this method involves inserting into the genome of the plant a DNA sequence coding for a compound of this invention in proper reading frame, together with transcription initiator and promoter sequences active in the plant. Transcription and translation of the DNA sequence under control of the regulatory sequences causes expression of the protein sequence at levels which provide an elevated amount of the protein in the tissues of the plant.

Preferred plants that are to be transformed according to the methods of this invention are cereal crops, including maize, rye, barley, wheat, sorghum, oats, millet, rice, triticale, sunflower, alfalfa, rapeseed and soybean. Synthetic DNA sequences can then be prepared which code for the appropriate sequence of amino acids, and this synthetic DNA sequence can be inserted into an appropriate plant expression cassette.

Likewise, numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence.

In addition, the plant expression cassette preferably includes a strong constitutive promoter sequence at one end to cause the gene to be transcribed at a high frequency, and a poly-A recognition sequence at the other end for proper processing and transport of the messenger RNA. An example of such a preferred (empty) expression cassette into which the cDNA of the present invention can be inserted is the pPHI414 plasmid developed by Beach, et al., of Pioneer Hi-Bred International, Inc., Johnston, IA, as disclosed in U.S. patent application No. 07/785,648; (1991); incorporated herein in its entirety by reference. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

As mentioned above, both genomic and cDNA encoding the gene of interest may be used in this invention. The vector of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a first genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

Promoters that may be used in the genetic sequence include NOS, OCS and CaMV promoters.

An efficient plant promoter that may be used is an overproducing plant promoter. Overproducing plant promoters that may be used in this invention include the promoter of the cholorophyll $\alpha$-$\beta$ binding protein, and the promoter of the small sub-unit (sS) of the ribulose-1,5-biphosphate carboxylase from soybean. See e.g. Berry-Lowe, et al., *J. Molecular and App. Gen.;* Vol. 1; pp. 483–498; (1982); incorporated herein in its entirety by reference. These two promoters are known to be light-induced, in eukaryotic plant cells. See e.g., *An Agricultural Perspective*, A. Cashmore, Pelham, New York, 1983, pp. 29–38, G. Coruzzi, et al., *J. Biol. Chem.,* Vol. 258; p. 1399 (1983), and P. Dunsmuir, et al., *J. Molecular and App. Gen.,* Vol. 2; p. 285 (1983); all incorporated herein in their entirety by reference.

The expression cassette comprising the structural gene for the protein of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. typhimurium,* and *Serratia marcescens.* Eukaryotic hosts such as yeast or filamentous fungi may also be used in this invention. Since these hosts are also microorganisms, it will be essential to ensure that plant promoters which do not cause expression of the protein in bacteria are used in the vector.

The isolated cloning vector will then be introduced into the plant cell using any convenient technique, including electroporation (in protoplasts), retroviruses, bombardment, and microinjection into cells from monocotyledonous or dicotyledonous plants in cell or tissue culture to provide transformed plant cells containing as foreign DNA at least one copy of the DNA sequence of the plant expression cassette.

Preferably, the monocotyledonous species will be selected from maize, sorghum, wheat or rice, and the dicotyledonous species will be selected from soybean, alfalfa, rapeseed, sunflower or tomato. Using known techniques, protoplasts can be regenerated and cell or tissue culture can be regenerated to form whole fertile plants which carry and express the gene for a protein according to this invention. Accordingly, a highly preferred embodiment of the present invention is a transformed maize plant, the cells of which contain as foreign DNA at least one copy of the DNA sequence of an expression cassette of this invention.

Finally, this invention provides methods of imparting resistance to diseases caused by microorganisms selected from *Fusarium graminearum, Fusarium moniliforme, Diplodia maydis, Collectototrichum graminicola, Verticillium alboatrum, Phytophthora megaspermae f.sp. glycinea, Macrophomina phaseolina, Diaporthe phaseolorum caulivora, Sclerotinia sclerotiorum, Sclerotinia trifoliorum, Aspergillus falvus* to plants of a susceptible taxon, comprising the steps of:

a) culturing cells or tissues from at least one plant from the taxon, b) introducing into the cells or tissue culture at least one copy of an expression cassette comprising a structural gene for one or more of the compounds of this invention, operably linked to plant regulatory sequences which cause the expression of the compound or compounds in the cells, and c) regenerating disease-resistant whole plants from the cell or tissue culture. Once plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the structural gene for the compound of this invention and associated regulatory sequences via crossing and backcrossing. Such intermediate methods will comprise the further steps of:

a) sexually crossing the disease-resistant plant with a plant from the disease-susceptible taxon;

b) recovering reproductive material from the progeny of the cross; and c) growing disease-resistant plants from the reproductive material. Where desirable or necessary, the agronomic characteristics of the susceptible taxon can be substantially preserved by expanding this method to include the further steps of repetitively:

a) backcrossing the disease-resistant progeny with disease-susceptible plants from the susceptible taxon; and b) selecting for expression of anti-microbial activity (or an associated marker gene) among the progeny of the backcross, until the desired percentage of the characteristics of the susceptible taxon are present in the progeny along with the gene imparting anti-microbial activity.

By the term "taxon" herein is meant a unit of botanical classification of genus or lower. It thus includes genus, species, cultivars, varieties, variants, and other minor taxonomic groups which lack a consistent nomenclature.

As used herein "pathogen" means any organism, bacterial or fungal, capable of causing disease in plants.

As used herein "anti-pathogenic" or "anti-microbial" activity means activity to prevent and/or combat and/or alleviate infection by a pathogen.

By "anti-microbial amount" herein is meant an amount of either polypeptide or combination thereof sufficient to provide anti-microbial activity so as to alleviate or prevent infection by susceptible organisms in the plant at a reasonable benefit/risk ratio.

It will also be appreciated by those of ordinary skill that the plant vectors provided herein can be incorporated into *Agrobacterium tumefaciens*, which can then be used to transfer the vector into susceptible plant cells, primarily from dicotyledonous species. Thus, this invention provides a method for increasing methionine levels in *Agrobacterium tumefaciens*-susceptible dicotyledonous plants in which the expression cassette is introduced into the cells by infecting the cells with *agrobacterium tumefaciens*, a plasmid of which has been modified to include a plant expression cassette of this invention.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What is claimed is:

1. A method for killing and inhibiting plant pathogenic microorganisms which are susceptible to a α-Hordothionin comprising introducing into the environment of the pathogenic microorganisms an anti-microbial amount of a protein having the sequence of SEQUENCE I.D. NO. 3 wherein the amino acid residues at one or more of positions 1,5,8,11, 15,17,18,19,22,23,24,30,32, 33,38, and 41 are methionine, and the remainder of the residues at those positions are the residues at the corresponding positions in SEQUENCE I.D. NO. 1.

2. The method of claim 1 wherein one or more of the amino acid residues at positions 8,11,15,18,22,33, and 41 are methionine.

3. The method of claim 2 wherein at least three of the amino acid residues at positions 8,11,15,18,22,33, and 41 are methionine.

4. The method of claim 3 wherein at least five of the amino acid residues at positions 8,11,15,18,22,33, and 41 are methionine.

5. The method of claim 4 wherein the environment of the pathogen is the tissues of a living plant.

6. A method for killing and inhibiting plant pathogens selected from *Fusarinm graminearum, Fusarinm moniliforme, Diplodia maydis, Colletototrichnm graminicola, Verticillium alboatrum, Phytophthora megaspermae f.sp. glycinea, Macrophomina phaseolina, Diaporthe phaseolorum cavlivora, Sclerotinia sclerotiornm, Sclerotinia trifoliorum,* and *Aspergillus flavus*, comprising introducing into the environment of the pathogenic microorganisms an anti-microbial amount of a protein having the sequence of SEQUENCE I.D. NO. 3 wherein the amino acid residues at one or more of positions 1,5,8, 11,15,17,18,19, 22,23,24,30,32,33,38, and 41 are methionine, and the remainder of the residues at those positions are the residues at the corresponding positions in SEQUENCE I.D. NO. 1.

7. The method of claim 6 wherein the environment of the pathogen is the tissues of a living plant.

8. The method of claim 7 wherein one or more of the amino acid residues at positions 8,11,15,18,22,33, and 41 are methionine.

9. The method of claim 8 wherein at least three of the amino acid residues at positions 8,11,15,18,22,33, and 41 are methionine.

10. The method of claim 9 wherein at least five of the amino acid residues at positions 8,11,15,18,22,33, and 41 are methionine.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( D ) TOPOLOGY: linear ( x i ) SEQUENCE DESCRIPTION: SEQ ID NO:1:

```
Lys Ser Cys Cys Arg Ser Thr Leu Gly Arg Asn Cys Tyr Asn Leu Cys
 1               5                  10                  15
Arg Val Arg Gly Ala Gln Lys Leu Cys Ala Gly Val Cys Arg Cys Lys
            20                  25                  30
Leu Thr Ser Ser Gly Lys Cys Pro Thr Gly Phe Pro Lys
        35                  40              45
```

( 2 ) INFORMATION FOR SEQ ID NO:2:

(i) SEQUENCE CHARACTERISTICS:
   (A) LENGTH: 45 amino acids
   (B) TYPE: amino acid
   (D) TOPOLOGY: linear (xi) SEQUENCE DESCRIPTION: SEQ ID NO:2:

```
Lys Ser Cys Cys Arg Ser Thr Met Gly Arg Met Cys Tyr Asn Met Cys
1               5                   10                  15

Arg Met Arg Gly Ala Met Lys Leu Cys Ala Gly Val Cys Arg Cys Lys
            20                  25                  30

Met Thr Ser Ser Gly Lys Cys Pro Met Gly Phe Pro Lys
        35                  40                  45
```

(2) INFORMATION FOR SEQ ID NO:3:

(i) SEQUENCE CHARACTERISTICS:
   (A) LENGTH: 45 amino acids
   (B) TYPE: amino acid
   (D) TOPOLOGY: linear (xi) SEQUENCE DESCRIPTION: SEQ ID NO:3:

```
Met Ser Cys Cys Met Ser Thr Met Gly Arg Met Cys Tyr Asn Met Cys
1               5                   10                  15

Met Met Met Gly Ala Met Met Met Cys Ala Gly Val Cys Met Cys Met
            20                  25                  30

Met Thr Ser Ser Gly Met Cys Pro Met Gly Phe Pro Lys
        35                  40                  45
```